(12) United States Patent
Kurosaka (10) Patent No.: US 8,449,826 B2
(45) Date of Patent: May 28, 2013

(54) DETECTION DEVICE

(75) Inventor: Ryoji Kurosaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 1033 days.

(21) Appl. No.: 11/955,286

(22) Filed: Dec. 12, 2007

(65) Prior Publication Data

US 2008/0238571 A1 Oct. 2, 2008

(30) Foreign Application Priority Data

Dec. 20, 2006 (JP) .................................. 2006-343051

(51) Int. Cl.
*G01N 21/00* (2006.01)

(52) U.S. Cl.
USPC .................... 422/82.11; 333/17.1; 333/219.1; 333/235; 333/240; 250/339.01; 250/340; 422/50; 422/82.01; 422/82.05; 324/663; 324/615; 324/341

(58) Field of Classification Search
USPC ................ 333/17.1, 219.1, 235; 250/339.05, 250/341.8; 422/50, 82.01, 82.05, 82.11
See application file for complete search history.

(56) References Cited

U.S. PATENT DOCUMENTS

| | | | |
|---|---|---|---|
| 6,485,905 B2 * | 11/2002 | Hefti | 435/6 |
| 2005/0233490 A1 | 10/2005 | Kasai et al. | 438/46 |
| 2006/0085160 A1 | 4/2006 | Ouchi | 702/150 |

FOREIGN PATENT DOCUMENTS

| | | |
|---|---|---|
| JP | 9-43141 | 2/1997 |
| JP | 2001-13087 | 1/2001 |
| JP | 2005-17644 | 1/2005 |
| JP | 2005-20304 | 1/2005 |
| JP | 2005-311310 | 11/2005 |
| JP | 2006-133088 | 5/2006 |
| JP | 2006-275592 | 10/2006 |

OTHER PUBLICATIONS

M. Nagel, et al., "Integrated THz technology for label-free genetic diagnosis", Applied Physics Letters, vol. 80, No. 1, Jan. 7, 2002, pp. 154-156.
J. Kitagawa, et al., "THz spectroscopic characterization of biomolecule/water systems by compact sensor chips", Applied Physics Letters, 89, 041114 (2006).
T. Ohkubo, et al., "Micro-strip-line-based sensing chips for characterization of polar liquids in terahertz regime", Applied Physics Letters, 88, 212511 (2006).
M. Nagel, et al., "A functionalized THz sensor for marker-free DNA analysis", Physics in Medicine and Biology, 48, pp. 3625-3636 (2003).

* cited by examiner

*Primary Examiner* — In Suk Bullock
*Assistant Examiner* — Robert Eom
(74) *Attorney, Agent, or Firm* — Fitzpatrick, Cella, Harper & Scinto (57) ABSTRACT

Since known detection devices include detectors of the same number as that of samples, the system configuration is complicated. According to the present invention, therefore, a plurality of electromagnetic-wave-transmission lines with different propagation-delay times and a coupled-transmission line coupling the electromagnetic-wave-transmission lines with each other are provided, and an electromagnetic wave is detected by the same electromagnetic-wave-detection unit. Subsequently, a detection device including at least one electromagnetic-wave detector of a number smaller than that of samples can be provided, which decreases the system complexity.

4 Claims, 11 Drawing Sheets

DETECTION DEVICE

BACKGROUND OF THE INVENTION

1. Field of the Invention

The present invention relates to a device configured to detect information relating to a sample by using an electromagnetic wave in the frequency band of 30 gigahertz (GHz) to 30 terahertz (THz).

2. Description of the Related Art

As a method, an apparatus, a device, etc. that are configured to generate and detect the frequency band of 30 GHz to 30 THz (hereinafter referred to as a terahertz wave) from a millimeter wave have been developed in recent years, technologies using terahertz waves receive attention. For example, the technology of performing imaging by using a safe fluoroscopic-inspection device in place of an X-ray machine, the spectroscopic technology of testing the bonding state by studying the absorption spectrum and/or complex permittivity of matter, the technology of analyzing a biomolecule, a communication technology, etc. have been studied and developed, as new application fields of the terahertz wave.

Figure 11:
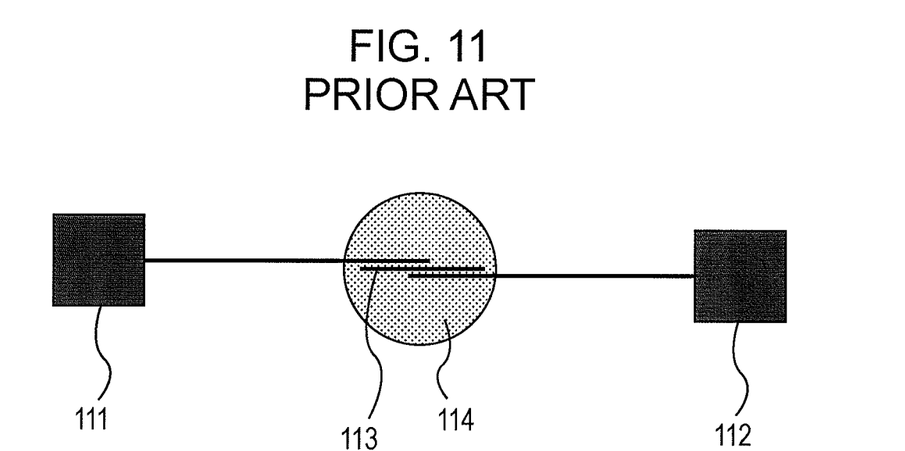
FIG. 11 shows a known technology.

FIG. 11 is a schematic diagram of a known technology relating to "Appl. Phys. Lett. 154, Vol 80, 2002", which is a paper on a transmission-line-type terahertz detector. As shown in FIG. 11, a transmission section is provided between a terahertz-wave-generation unit 111 and a terahertz-wave-detection unit 112, a filter unit 113 is provided in the part corresponding to the transmission section, and a solution 114 containing deoxyribonucleic acids (DNAs) is provided on the filter unit 113, where the DNA is a sample. The DNA is dropped on a transmission line, and the DNA is analyzed based on the difference between the signal of an electromagnetic wave propagated through the transmission line when the DNA is provided and the signal of an electromagnetic wave propagated through the transmission line when the DNA is not provided. That is to say, "Appl. Phys. Lett. 154, Vol 80, 2002" discloses that the difference between a single-stranded DNA and a double-stranded DNA is detected based on the difference between permittivities by using the transmission-line-type terahertz detector.

Further, Japanese Patent Laid-Open No. 2001-13087 discloses a transmission-line-type detector configured to calculate the water content of an object to be measured including soil, a solution, etc. An output end is divided into branches by using a microwave, and transmission lines with different lengths are provided. According to Japanese Patent Laid-Open No. 2001-13087, any of the transmission lines is selected in consideration of the propagation loss of an electromagnetic wave, and high to low degrees of water contents are calculated.

SUMMARY OF THE INVENTION

According to the above-described known technologies, the following problems arise when a plurality of samples is measured. For measuring the samples at one time by using a device disclosed in Japanese Patent Laid-Open No. 2001-13087, generation units, detection units, and filter units should be provided according to the number of samples. Further, the generation units, the detection units, and the filter units should be arrayed.

Further, when the device disclosed in Japanese Patent Laid-Open No. 2001-13087 is used to perform measurement by using a terahertz wave, a detection unit should be provided on each of output ends and the detection units should be arrayed, and the detection units should be provided according to the number of samples, which makes the system configuration complicated.

Accordingly, the present invention provides a detection device that can decrease the number of detection units used to detect a plurality of samples.

The present invention provides a detection device configured to detect a sample by using an electromagnetic wave in a frequency band of 30 gigahertz to 30 terahertz. The detection device includes a plurality of electromagnetic-wave-transmission lines, wherein at least two of the electromagnetic-wave-transmission lines have times of delay in propagation of the electromagnetic wave that are different from each other, a coupled-transmission line configured to transmit the electromagnetic waves propagated from the electromagnetic-wave-transmission lines to a single electromagnetic-wave-detection unit, and the electromagnetic-wave-detection unit, which is configured to detect the electromagnetic waves propagated through the coupled-transmission line. The electromagnetic-wave-transmission lines and the coupled-transmission line are formed on a substrate.

Thus, since the plurality of electromagnetic-wave-transmission lines with different propagation-delay times is provided, it becomes possible to perform detection by using the same electromagnetic-wave-detection unit via the coupled-transmission line. Subsequently, it becomes possible to detect a plurality of samples and/or a sample and a reference by using electromagnetic-wave-detection units of a number smaller than that of the samples.

Further features of the present invention will become apparent from the following description of exemplary embodiments with reference to the attached drawings.

DESCRIPTION OF EXAMPLE EMBODIMENTS

Figure 1:
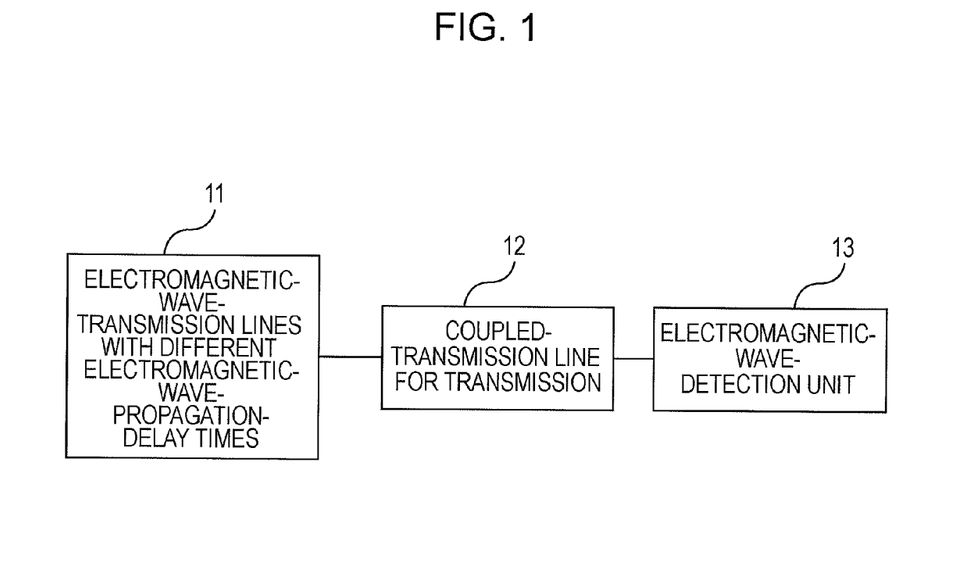
FIG. 1 is a conceptual illustration of an embodiment of the present invention.

FIG. 1 shows a structure according to an embodiment of the present invention. The structure includes a plurality of electromagnetic-wave-transmission lines 11, where the times of delay in electromagnetic-wave propagation of the electromagnetic-wave-transmission lines 11 are different from one another. The structure further includes a coupled-transmission line 12 configured to transmit electromagnetic waves propagated through a plurality of electromagnetic-wave-propagation paths to the same electromagnetic-wave-detection unit 13.

Namely, according to an embodiment of the present invention, a plurality of electromagnetic-wave-transmission lines with different delay times is provided. The delay times of some of the electromagnetic-wave-transmission lines may be the same with each other.

The above-described structure shown in FIG. 1 may be used as a replaceable chip. Of course, the above-described structure shown in FIG. 1 may be used as a stationary measuring device. Further, an electromagnetic-wave-generation unit configured to generate an electromagnetic wave and/or an electromagnetic-wave-coupling unit configured to couple propagated electromagnetic waves with each other may be added to the above-described structure, and a liquid-storage structure may be provided on the transmission line, as an auxiliary used to deposit samples selectively and/or avoid the liquid leakage. Still further, it is also possible to generate a selective set of samples by modifying the surface of the transmission line and/or the surface of the neighborhood of the transmission line, so as to selectively gather the samples on the transmission line. The above-described structures may be integrated on the same substrate so that a chip is achieved.

For changing the propagation-delay time, a section configured to change the length of time that an electromagnetic wave propagates by changing the length of the transmission line and a section configured to change the length of the time that the electromagnetic wave propagates by changing the permittivity of a dielectric forming the electromagnetic-wave-transmission line 11 can be provided. By providing the electromagnetic-wave-transmission lines with different propagation-delay times, the signals of a plurality of samples can be detected in real time so that measurement can be performed with high precision.

Figure 2:
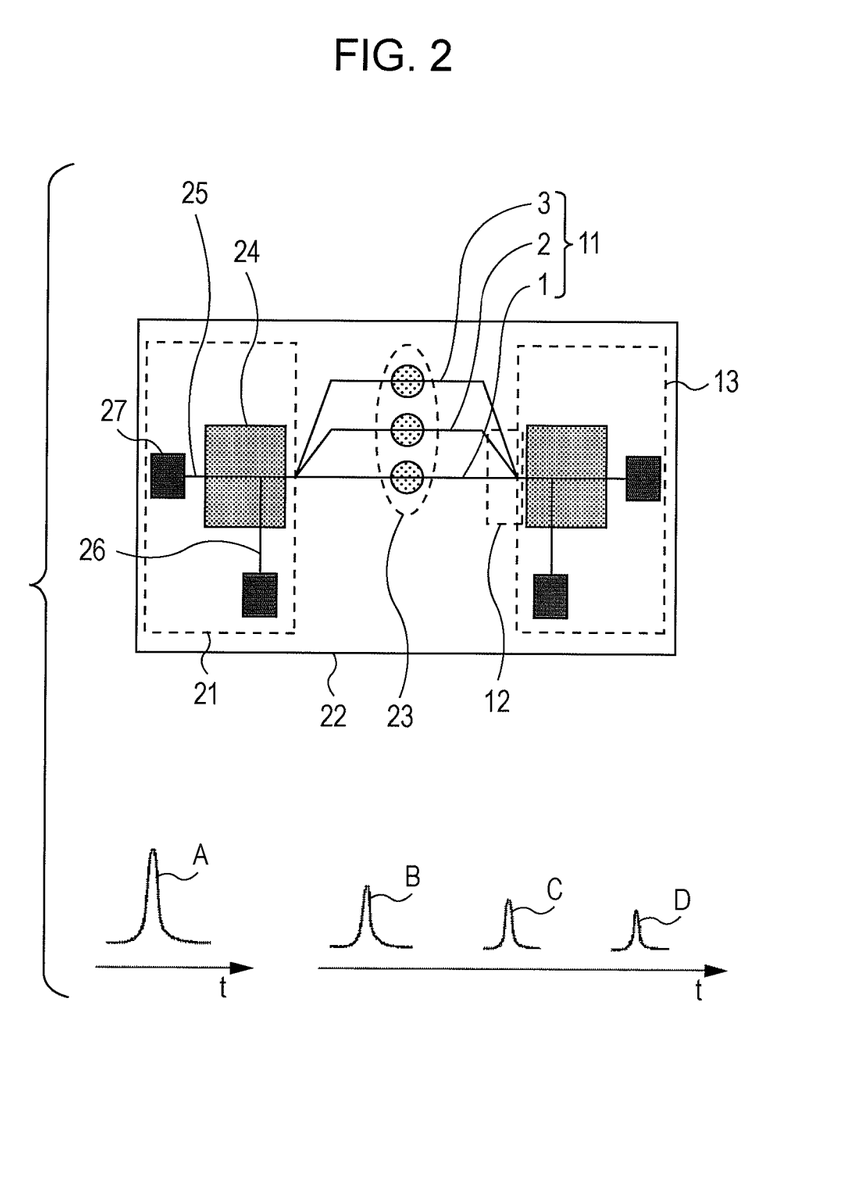
FIG. 2 shows another embodiment of the present invention.

The principle of detection will be described with reference to FIG. 2 showing another embodiment of the present invention.

According to the embodiment shown in FIG. 2, an electromagnetic-wave-generation unit 21 is formed on a substrate 22 in advance. Terahertz waves generated from the electromagnetic-wave-generation unit 21 are propagated through a plurality of electromagnetic-wave-transmission lines with different propagation-delay times. According to the embodiment shown in FIG. 2, a transmission line is divided into branches and the terahertz waves are propagated through electromagnetic-wave-transmission lines 1, 2, and 3. A sample 23 is provided in each of the electromagnetic-wave-transmission lines 1, 2, and 3. As shown in FIG. 2, the electromagnetic-wave-transmission line 1 is the shortest of the above-described electromagnetic-wave-transmission lines. The second shortest of the above-described electromagnetic-wave-transmission lines is the electromagnetic-wave-transmission line 2, and the longest of the above-described electromagnetic-wave-transmission lines is the electromagnetic-wave-transmission line 3. Then, the electromagnetic wave of each of the terahertz waves propagated through the electromagnetic-wave-transmission lines 1, 2, and 3 is propagated through the coupled-transmission line 12, and detected by the same electromagnetic-wave-detection unit 13.

In that case, a terahertz wave is generated by the electromagnetic-wave-generation unit 21 and propagated through the transmission line. If a pulse-like terahertz wave is generated at that time, the signal of the generated terahertz wave becomes as signal A shown in FIG. 2. The signal A is propagated through the transmission line and branched at the plurality of electromagnetic-wave-transmission lines, and propagated. At that time, the lengths of the electromagnetic-wave-transmission lines through which the terahertz waves are propagated are different from one another. Therefore, signals which arrive at the coupled-transmission line are temporally different from one another. Since the length of the electromagnetic-wave-transmission line 1 is the shortest, a signal propagated through the electromagnetic-wave-transmission line 1 arrives at the coupled-transmission line ahead of other signals propagated through the electromagnetic-wave-transmission line 2 and 3. Further, the signal propagated through the longest electromagnetic-wave-transmission line 3 arrives at the coupled-transmission line after the signals propagated through the electromagnetic-wave-transmission lines 1 and 2. The electromagnetic-wave-detection unit 13 detects the above-described signals so that the signals corresponding to the samples can be detected in real time, which makes it possible to perform measurement with high precision.

The detected signals are output, as signals B, C, and D, as shown in FIG. 2. In FIG. 2, an output signal propagated through the shortest electromagnetic-wave-transmission line 1 becomes the signal B, and an output signal propagated through the longest electromagnetic-wave-transmission line 3 becomes the signal D. The signal of the electromagnetic-wave-transmission line 2 standing midway between the electromagnetic-wave-transmission lines 1 and 3 becomes the signal C standing midway between the signals B and D. Each of the above-described signals B, C, and D is affected by the interaction between the terahertz wave and the sample. Therefore, the propagation state of the transmitted terahertz wave is changed due to the interaction between the terahertz wave and the sample, etc., which makes it possible to determine what sample is provided by analyzing the change based on the signal. According to the above-described detection, it becomes possible to measure a protein or the like before the protein changes over time, where the conformation of protein changes due to denaturation or the like, so that detection can be performed with higher precision. It is also possible to observe the protein or the like changing over time and detect the denaturation degree.

Figure 3:
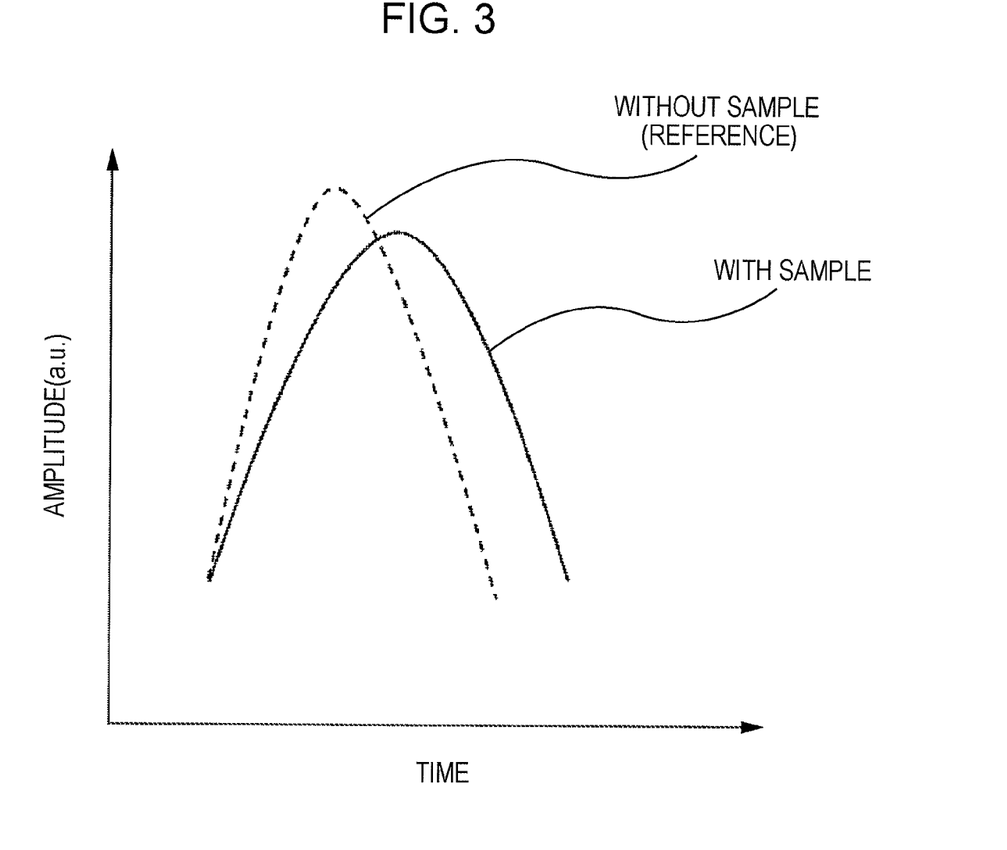
FIG. 3 shows detectable signals.

More specifically, a terahertz wave is generated before providing a sample, the terahertz wave is detected by the electromagnetic-wave-detection unit 13, and data on the time waveform of the detected terahertz wave is stored. Next, a terahertz wave is generated after providing the sample, the terahertz wave is detected by the electromagnetic-wave-detection unit 13, and data on the time waveform of the detected terahertz wave is stored. FIG. 3 shows the time waveforms obtained in the above-described manner. As shown in FIG. 3, there is a difference between the signal waveform obtained when the sample is provided and that obtained when the sample is not provided, where the difference is caused due to a time delay and/or the attenuation of a pulse peak which occurs when the terahertz wave is affected by the macroscopic complex permittivity of the sample. The property of the sample can be measured by analyzing the above-described information.

Figure 4:
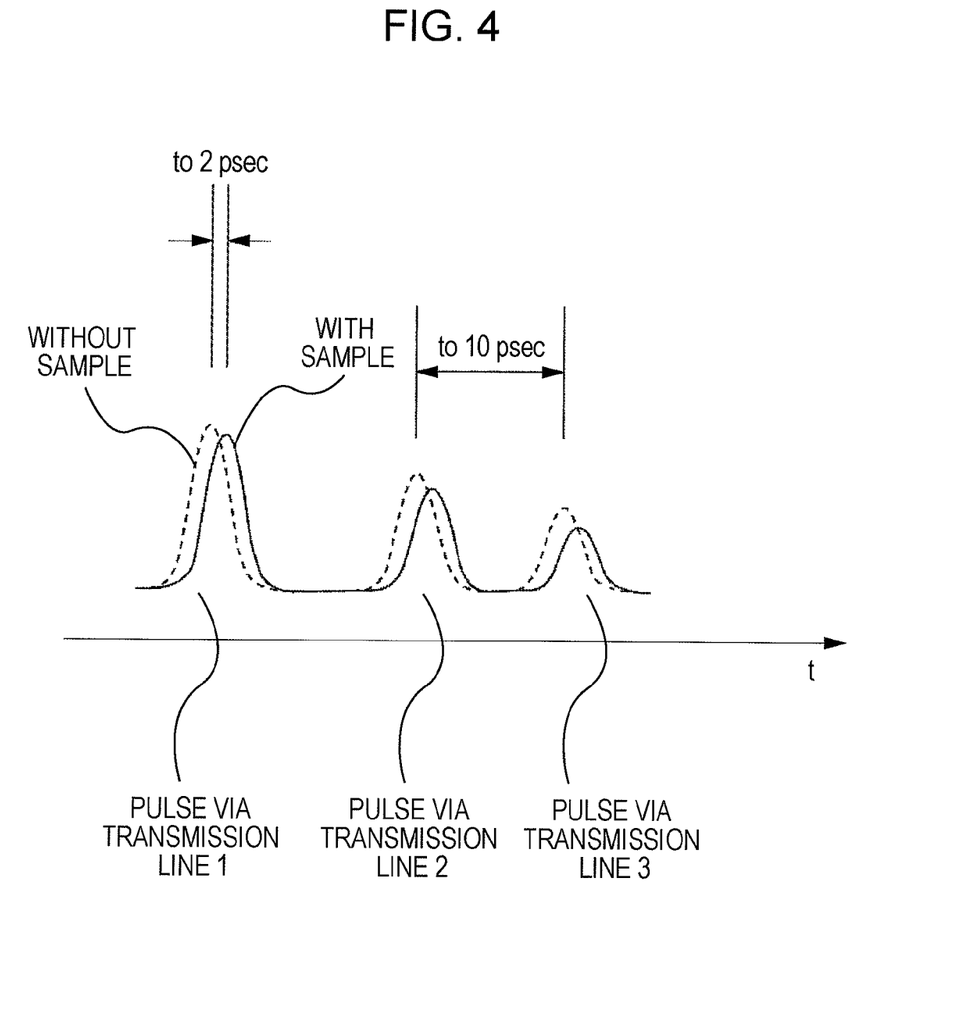
FIG. 4 shows signals that can be detected according to the configuration shown in FIG. 2.

When the measurement according to the embodiment shown in FIG. 2 is performed, signals shown in FIG. 4 can be obtained, for example. In FIG. 4, each of the signals denotes output data on a time waveform. The sample-occupation area provided on the transmission line, and the presence or absence of the sample cause a difference between the peak intensity of the waveform of one of the signals and that of the waveform of the other signal and/or a difference between the time difference between the waveform peaks of one of the signals and that between the waveform peaks of the other signal. Subsequently, it becomes possible to analyze the sample based on the above-described difference. For example, it becomes possible to identify a double-stranded DNA or a single-stranded DNA. It becomes possible to detect the time difference between the signal of a reference and the signal of a measured sample in the order of from sub psec to psec for the drop amount of several tens of nanoliters (nl) of solution containing DNAs. Further, the measured time waveform is separated into pulses and each of the pulses is subjected to Fourier transform. Subsequently, it becomes possible to obtain the frequency spectrum achieved when the sample is provided and the frequency spectrum achieved when the sample is not provided. By using the above-described frequency spectrums, the sample is analyzed based on an attenuation and/or an absorption peak.

Further, there is a method of detecting the reference signal and the sample signal at the same time without measuring the reference and storing data on the reference. The above-described method will be described with reference to FIG. 5, for example. The reference-transmission lines 51 corresponding to the electromagnetic-wave-transmission lines 11 with different electromagnetic-wave-propagation-delay times are provided, so as to measure a plurality of samples and a reference at the same time. Each of the electromagnetic-wave-transmission lines 11 and the reference-transmission lines 51 is integrated on the same substrate, that is, the substrate 22. More specifically, four lines are provided, so as to measure two types of samples 23, where the four lines include an electromagnetic-wave-transmission line used for sample A, an electromagnetic-wave-transmission line used for sample B, an electromagnetic-wave-transmission line used for sample-A reference, and an electromagnetic-wave-transmission line used for sample-B reference.

Figure 6:
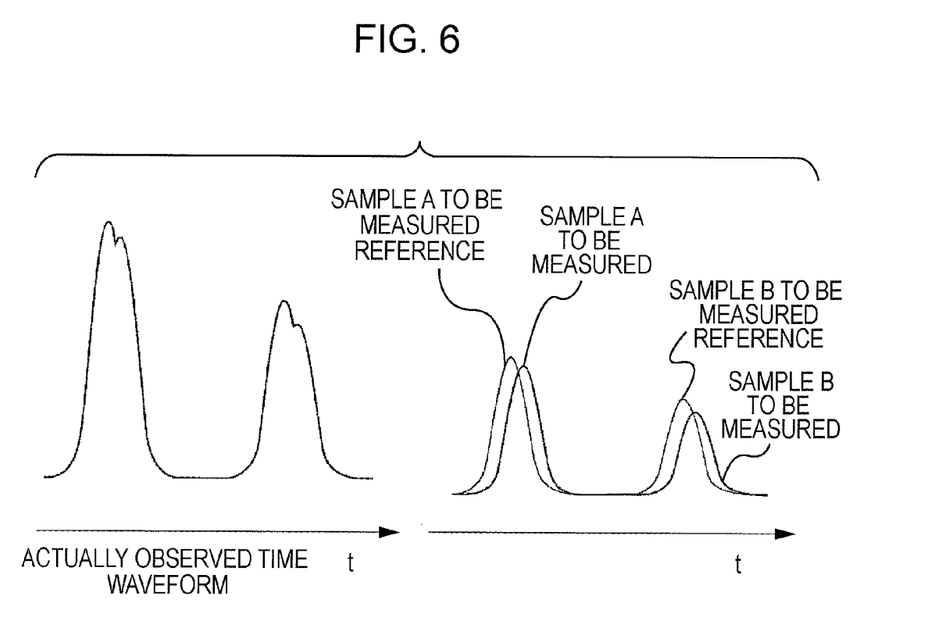
FIG. 6 shows signals that can be detected according to the configuration shown in FIG. 5.

In FIG. 6, the electromagnetic-wave-transmission lines are provided, so as to be symmetrical about the center line of a transmission-line substrate. One of the transmission lines of the same length is used for the sample and the other is used for the reference. The length of the sample-A-electromagnetic-wave-transmission line is determined to be the same as that of the sample-A-reference-electromagnetic-wave-transmission line, and a signal transmitted from the sample-A-electromagnetic-wave-transmission line is compared to that transmitted from the sample-A-reference-electromagnetic-wave-transmission line. Subsequently, it becomes possible to detect a signal by which the characteristic of the sample A can be analyzed based on the difference between the pulse-peak intensity of the reference signal and that of the measured-sample signal, and the difference between the time delay of the reference signal and that of the measured-sample signal, as shown in FIG. 6. By comparing the sample to the reference on every occasion in the above-described manner, the measurement precision can be increased.

Next, each of the above-described components will be described specifically.

(Electromagnetic-Wave-Transmission Line)

A. Electromagnetic-Wave-Transmission Line

A microstripline can be used, as the electromagnetic-wave-transmission line, as is the case with FIG. 2. The microstripline includes two metal layers and a dielectric provided therebetween. The metal layers are formed by stacking Ti/Au on each other, and a dielectric layer includes benzocyclobutene (hereinafter referred to as BCB), as a dielectric material. BCB is relatively transparent in the terahertz-wave area, easy to machine such as etching, and has fine chemical resistance. Otherwise, the dielectric material may be polysilane, polyimide, Teflon (registered trademark), polyolefin, and SU-8. Since the above-described microstripline has a low terahertz-wave-propagation loss and a fine dispersion characteristic, an electromagnetic wave can be confined in the transmission line. However, if a plurality of samples can be provided, the strip-line structure should be used. Further, a coplanar-strip-line structure and/or a coplanar-waveguide structure, which is a coplanar structure, may be used.

A method of forming a transmission line such as the microstripline is disclosed in Japanese Patent Laid-Open No. 2005-17644, Japanese Patent Laid-Open No. 2005-20304, and US 2006/0085160, for example. The method can be used for the present invention.

B. Propagation-Delay Structure

For delaying the propagation of an electromagnetic wave, the transmission lines with different lengths may be provided, as is the case with FIG. 2. In a vacuum, it takes three picoseconds (psecs) to propagate the electromagnetic wave of a terahertz wave by as much as one millimeter. When the electromagnetic wave is propagated through a transmission line including a dielectric, the propagation delay occurs according to the effective permittivity of the dielectric. Therefore, for temporally separating the terahertz wave of several psecs, the length of the electromagnetic-wave-transmission line is changed in mm order. For example, if the length of the electromagnetic-wave-transmission line 1 is determined to be 1 mm, the length of the electromagnetic-wave-transmission line 2 is determined to be 2 mm, and the length of the electromagnetic-wave-transmission line 3 is determined to be 3 mm, the signal separation can be performed in psec. If the dielectric includes BCB, the peak of the signal waveform differs by as much as about 5 psecs each time the transmission length differs by as much as one millimeter in consideration of the permittivity of BCB.

Figure 7A:
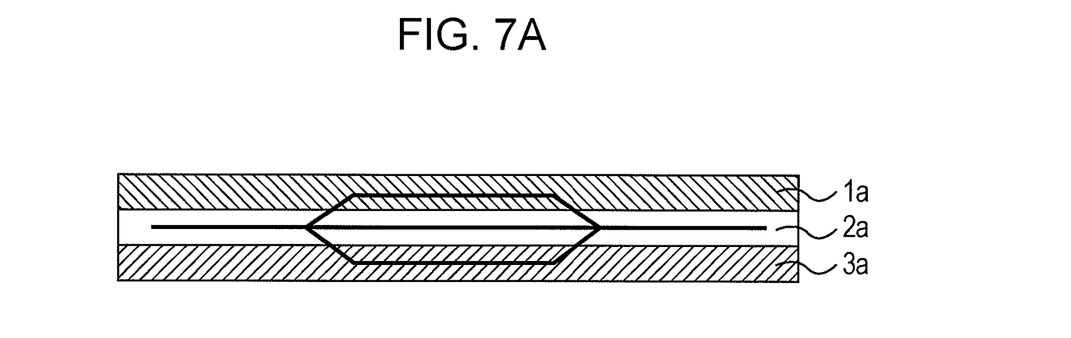
FIG. 7A shows dielectric materials according to another embodiment of the present invention.

Further, other than the method of changing the transmission-line length, a method of changing the type of materials constituting the electromagnetic-wave-transmission line may be used. In many cases, the dielectric type is changed in place of changing the metal-layer type. For decreasing the time required to detect an electromagnetic wave, that is to say, for reducing the propagation time, a low-permittivity material is used. On the other hand, a high-permittivity material is used so as to increase the time required to detect the electromagnetic wave. For example, dielectrics 1a, 2a, and 3a with different permittivities may be used in combination, so as to manufacture the dielectric part, as shown in FIG. 7A. It is preferable that each of the dielectrics 1a, 2a, and 3a includes a material transparent to a terahertz wave. Since the delay time of the electromagnetic-wave propagation changes due to a change in the permittivity, a signal is separated in time based on the time where an electromagnetic wave is coupled with the coupled-transmission line 12. By changing the dielectric, the signal waveform of the terahertz wave can be separated without changing the transmission-line length.

Figure 7B:
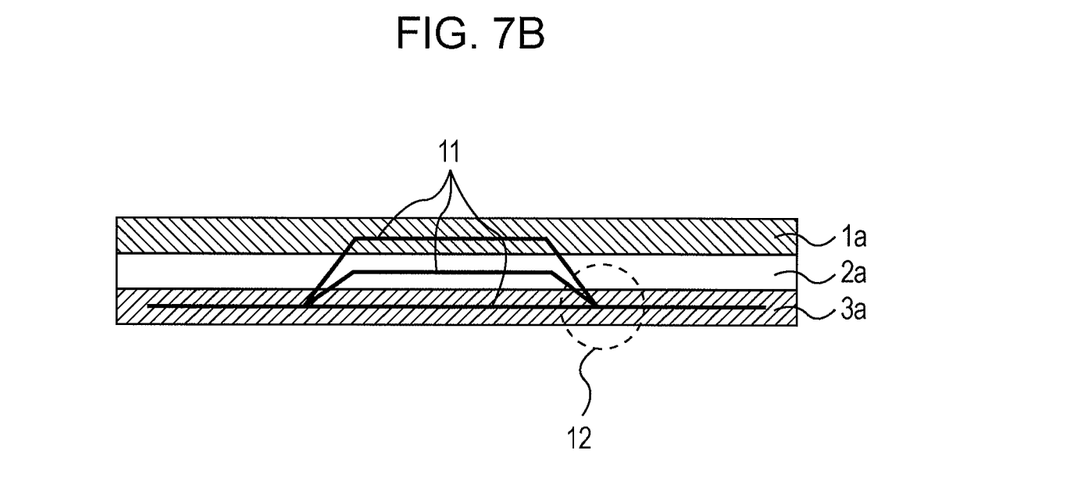
FIG. 7B shows dielectric materials according to another embodiment of the present invention.

Of course, the above-described two methods may be used in combination so that electromagnetic-wave-transmission lines are formed on a substrate, as shown in FIG. 7B. By using the above-described two methods in combination, the signal separation can be performed in a sophisticated manner.

C. Arrangement of Samples on Electromagnetic-Wave-Transmission Lines

For achieving the interaction between the terahertz wave and the sample more effectively, the sample should be arranged in the electromagnetic-wave-transmission line appropriately. The sample may be biological matter including a DNA, amino acid, a protein, etc. The biological matter often includes absorption unique to the biological matter in the frequency area of the terahertz wave. Therefore, the analysis of the peak of absorption allows for detecting the biological matter itself and/or measuring the degree of denaturation of the biological matter. For arranging the samples, a solution is dropped on the transmission line, and the solution is dried so that samples included in the solution are deposited. For analyzing a DNA, the amount of DNAs included in a phosphate-buffer solution is adjusted so that the concentration of DNAs of the phosphate-buffer solution is expressed, as 0.5 µg/µl. The adjusted phosphate-buffer solution is dropped on the transmission line, and subjected to air drying so that the samples are immobilized and deposited. The adjusted phosphate-buffer solution is sequentially dropped on branch transmission lines formed by dividing a single transmission line into branches, and the phosphate-buffer solution is dried. At that time, care should be taken to see that the samples do not overlap one another.

However, if solutions including the samples are simply dropped on the electromagnetic-wave-transmission line, the solutions are often mixed with each other. In that case, the following structure may be used, as an option provided to achieve the sample arrangement, so as to measure the samples more correctly.

C-1. Liquid-Storage Structure

Figure 10:
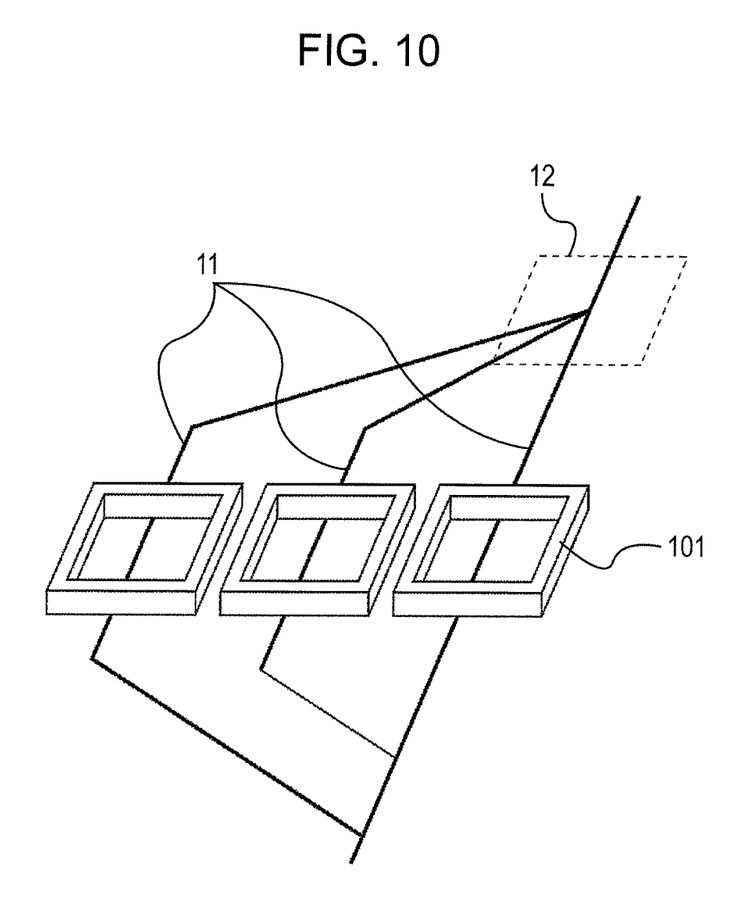
FIG. 10 shows a liquid-storage structure according to an embodiment of the present invention.

For detecting biological matter including a DNA, a protein, etc., the biological matter is dissolved in a solution such as a buffer solution in consideration of the stability of the biological matter. In the case where the above-described solution is used, a liquid-storage structure 101 shown in FIG. 10 may be provided, so as to prevent a liquid from being spread out on a substrate. The liquid-storage structure 101 includes a wall surrounding an area on which the liquid is dropped. Subsequently, it becomes possible to precipitate and deposit the biological matter at a predetermined position on an electromagnetic-wave-transmission line, and prevent the biological matter from being mixed with different biological matter. Further, the liquid-storage structure 101 prevents the biological matter from being mixed with a specimen for measurement, where the specimen is arranged on a different electromagnetic-wave-transmission line, so that the biological matter can be measured with high precision. Further, since the liquid-storage structure 101 is shaped, as shown in FIG. 10, the solution amount can be specified so that the quantitative property increases.

The liquid-storage structure is manufactured by applying and baking a material that is transparent to a terahertz wave and that is used to form the wall of the liquid-storage structure on an electromagnetic-wave-transmission line prepared by evaporation. Then, after patterning a masking material, etching is performed while leaving the part corresponding to the wall of the liquid-storage structure, whereby the liquid-storage structure is formed.

On the other hand, a hole may be formed instead of the wall, so as to be used as the liquid-storage structure. The hole may be formed in the direction that penetrates the metal layer, the dielectric, and the other metal layer so that a sample can be held in the hole.

C-2. Surface Modification

The type of a sample arranged on an electromagnetic-wave-transmission line can be selected by modifying the surface of the electromagnetic-wave-transmission line. More specifically, the sample type can be selected by introducing a functional group including an amino group, a carboxyl group, a hydroxyl group, a thiol group, a maleimido group, etc. on the surface of the electromagnetic-wave-transmission line. For example, the surface of a metal layer of an electromagnetic-wave-transmission line having two metal layers including the above-described metal layer and a dielectric provided therebetween can be modified by using the functional group, and nucleic acid including a DNA or the like can be selectively absorbed on the modified metal-layer surface. Further, by introducing different functional groups on the surfaces of the electromagnetic-wave-transmission lines, at least two DNAs dissolved in the same solution can be screened by using the functional groups so that the at least two DNAs can be detected. In that case, a solution containing two or more DNAs can be dropped on the entire face of the electromagnetic-wave-transmission line. Therefore, it is not necessary to drop two different solutions on the electromagnetic-wave-transmission line, which makes it possible to prevent the solutions from being mixed with each other.

The following method is used to immobilize a DNA and/or peptide-nucleic acid (PNA). Namely, the surface of Au forming a transmission line is modified by using a maleimido group so that the maleimido group reacts with the DNA and/or the PNA including a thiol group. Subsequently, the maleimido group and the thiol group are bonded to each other and immobilized. Further, a DNA and/or a PNA on which an alkyl chain (carbon number 5 to 18, preferably 12) is introduced can be immobilized on the transmission line. In that case, it becomes possible to introduce a probe including the DNAs and/or the PNAs on the transmission line by using hydrophobic packing so that the DNA and/or PNA density becomes higher than in the case where no alkyl chain is introduced. Subsequently, the above-described structure can be used as a DNA chip and/or a PNA chip. Although the surface of the electromagnetic-wave-transmission line is modified in the above-described embodiment, the thiol group or the like can be introduced on the end of a DNA and coupled with the electromagnetic-wave-transmission line. The idea of the surface modification can be applied not only to a plurality of electromagnetic-wave-transmission lines, but also to a known single transmission-line device.

(Coupled-Transmission Line)

The coupled-transmission line is configured to propagate terahertz waves propagated from the plurality of electromagnetic-wave-transmission lines to the electromagnetic-wave-detection unit. In the coupled-transmission line, the terahertz waves are combined with one another according to the propagation-delay time of each of the electromagnetic-wave-transmission lines and led to the same electromagnetic-wave-detection unit. For propagating the terahertz waves more correctly, the effect of reflection caused by an impedance mismatch should be reduced. Therefore, the coupled-transmission line may be shaped properly. For example, the coupled-transmission line may be formed as a T branch or a Y branch. In another embodiment, the width of the coupled-transmission line may be reduced immediately before a branch point.

(Electromagnetic-Wave-Detection Unit)

The electromagnetic-wave-detection unit is provided to detect a terahertz wave. More specifically, the electromagnetic-wave-detection unit may include, for example, a photoconductive element using GaAs grown at a low temperature, as a photoconductive film, a detector including electro-optic (EO) crystal, a bolometer, a superconducting-tunnel-junction element, or a Schottky diode. As for the above-described electromagnetic-wave-detection unit, it would be helpful to refer to Terahertz technology Development, Measurement, Application Technology, and Prospects~(Supervised by Toyoaki Oomori), Basics and Application of Terahertz wave (Written and Edited by Jun-ichi Nishizawa), Japanese Patent Laid-Open No. 2005-311310, and US 2005/0233490. Therefore, the description of the electromagnetic-wave-detection unit will not be provided.

(Electromagnetic-Wave-Generation Unit)

The electromagnetic-wave-generation unit may include a photoconductive element, which is often referred to as a photoconductive antenna and/or a photoconductive switch. The electromagnetic-wave-generation unit shown in FIG. 2 includes the photoconductive element. Further, the electromagnetic-wave-generation unit may include, for example, a backward-wave oscillator (BWO), a parametric generator, a quantum-cascade laser, a resonant-tunnel diode, etc. As for the above-described electromagnetic-wave-generation unit, it would be helpful to refer to Terahertz technology~Development, Measurement, Application Technology, and Prospects~(Supervised by Toyoaki Oomori), Basics and Application of Terahertz wave (Written and Edited by Jun-ichi Nishizawa), and Japanese Patent Laid-Open No. 2005-311310. Therefore, the description of the electromagnetic-wave-generation unit will not be provided.

Figure 5:
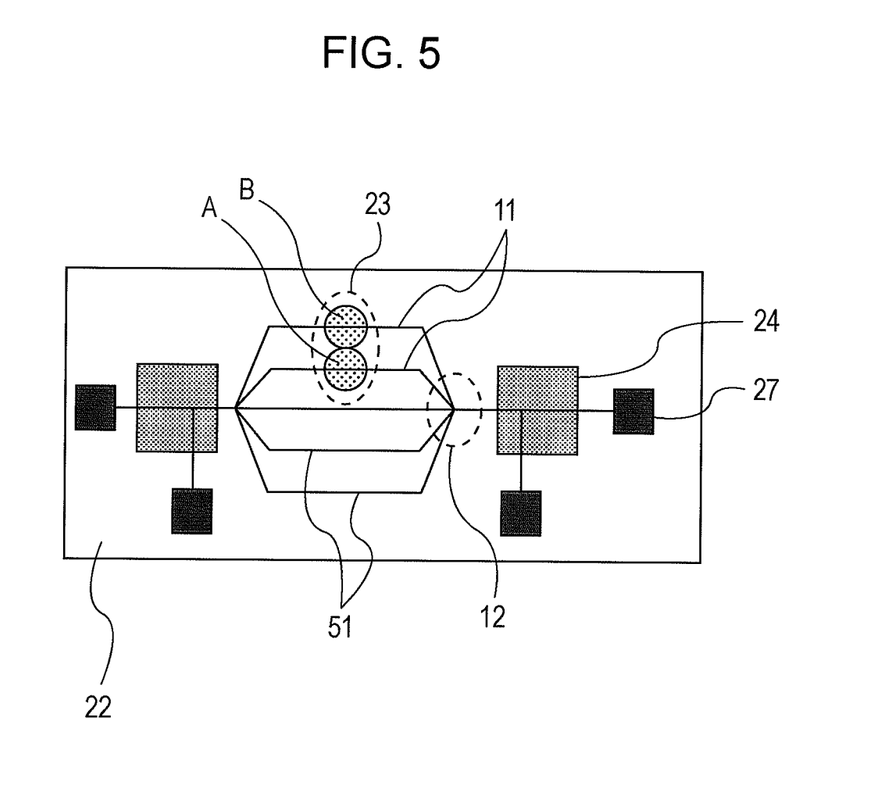
FIG. 5 shows a reference-transmission line according to another embodiment of the present invention.

Hereinafter, the photoconductive element used for the electromagnetic-wave-detection unit and the electromagnetic-wave-generation unit will be described with reference to the attached drawings. In the above-described embodiments of the present invention, a photoconductive element is used as the electromagnetic-wave-generation unit, as shown in FIGS. 2 and 5. In FIG. 2, a transmission line 25 is provided on a photoconductive film 24. Another transmission line 26 is provided at a distance of 5 μm from the transmission line 25 on the photoconductive film 24. Each of the above-described two transmission lines 25 and 26 functions, as an antenna and an electrode. For assuring the electrode function, an electrode pad 27 is provided at the end of each of the transmission lines 25 and 26, so as to apply a bias voltage to the photoconductive film 24. The photoconductive film 24 is irradiated with a laser (not shown) at the part corresponding to the distance between the transmission lines 25 and 26. Subsequently, a terahertz wave is generated from the photoconductive film 24.

Further, the electrodes may be arranged so that the bias voltage can be applied in the direction of the thickness of the photoconductive film 24. Thus, the direction in which the bias voltage is applied can be selected by device. For example, a photoconductive film is formed on a metal layer functioning as a ground (GND) layer, and BCB is stacked on the photoconductive film. After that, part of the stacked BCB is removed through patterning so that the photoconductive film is exposed. A transmission line connected to an electrode pad is provided on the photoconductive film. If BCB is stacked on the photoconductive film on a transmission line of 50Ω system so that the thickness of the stacked BCB becomes 5 μm, the metal width of the transmission line becomes 10 μm.

Particularly, when a terahertz wave is generated from a photoconductive element due to femtosecond laser excitation, the terahertz wave with the pulse width of several psecs is emitted after excitation is made by a femtosecond laser at the repetition frequency of several tens of MHz. That is to say, according to the time scale of the above-described structure, an electromagnetic wave with the pulse width of $10^{-12}$ seconds is emitted at time intervals of $10^{-8}$ seconds. Therefore, from the viewpoint of time, the terahertz wave exists in few areas. Namely, according to the above-described measurement method, a plurality of samples can be measured at the same time by effectively using the blank time areas, which is an appropriate application of the photoconductive element.

(Electromagnetic-Wave-Coupling Unit)

Figure 8:
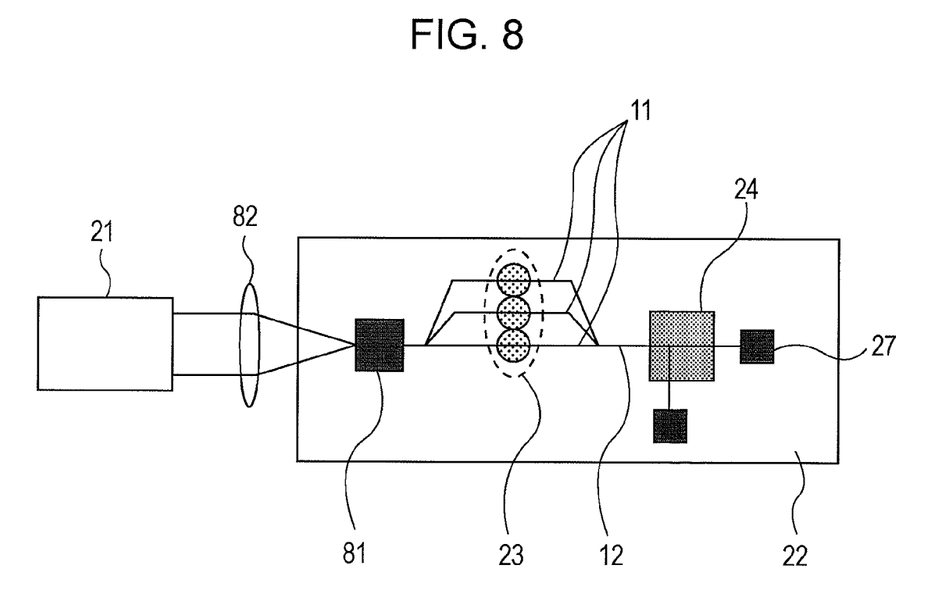
FIG. 8 shows an external-electromagnetic-wave generator according to another embodiment of the present invention.
Figure 9:
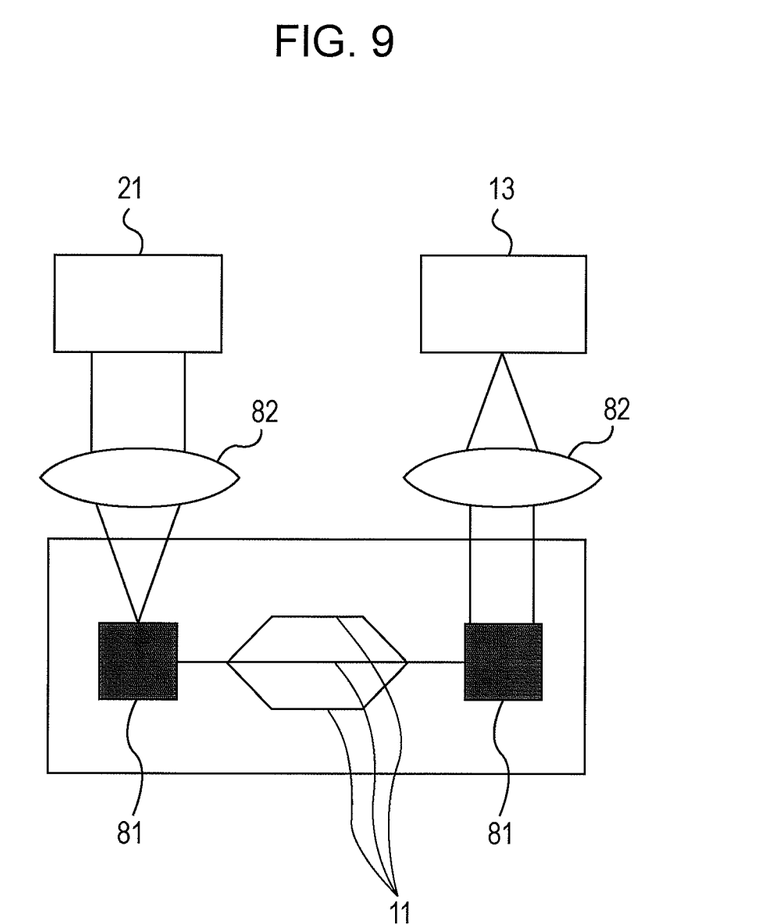
FIG. 9 shows a spatial coupler according to an embodiment of the present invention.

The electromagnetic-wave-coupling unit denotes an antenna used to couple electromagnetic waves with each other so that electromagnetic waves propagated through a free space are propagated to the electromagnetic-wave-transmission line. According to another embodiment of the present invention, a patch antenna shown in FIG. 8 is used. In that case, the electromagnetic-wave-generation unit may include a large sized electromagnetic-wave generator such as a BWO, which is integrated into a substrate with difficulty. Subsequently, the scope of application of the above-described structures increases. In FIG. 8, a patch antenna 81 is irradiated with condensed terahertz waves by using an optical system 82 configured to condense terahertz waves transmitted from an external electromagnetic-wave-generation unit 21. Although the electromagnetic-wave-generation unit shown in FIG. 8 is provided outside the structure, the electromagnetic-wave-detection unit 13 can also be provided outside the structure. Further, the electromagnetic-wave-generation unit 21 and the electromagnetic-wave-detection unit 13 can be provided outside the structure, as shown in FIG. 9. In that case, an inspection device including two electromagnetic-wave-coupling units, a plurality of electromagnetic-wave-transmission lines, and a coupled-transmission line that are provided on the same substrate is provided.

Thus, the structures according to the above-described embodiments allow for providing a detection device including a predetermined number of at least one electromagnetic-wave-detection unit, where the predetermined number is smaller than the number of samples. The detection device can be applied to an analyzer, a sensor configured to sense a sample such as blood sugar, and so forth.

In the above-described drawings, reference numeral 11 denotes the electromagnetic-wave-transmission line, reference numeral 12 denotes the coupled-transmission line, reference numeral 13 denotes the electromagnetic-wave-detection unit, and reference numeral 21 denotes the electromagnetic-wave-generation unit. Further, reference numeral 22 denotes the substrate. It is preferable that the above-described electromagnetic-wave-transmission lines and coupled-transmission line are formed on the same common substrate. Reference numeral 23 denotes the sample, reference numeral 24 denotes the photoconductive film, each of reference numerals 25 and 26 denotes the transmission line, and reference numeral 27 denotes the electrode pad.

Reference numeral 51 denotes the reference-transmission line, reference numeral 81 denotes the electromagnetic-wave-coupling unit, reference numeral 82 denotes a lens, reference numeral 101 denotes the liquid-storage structure, reference numeral 111 denotes the terahertz-wave-generation unit, reference numeral 112 denotes the terahertz-wave-detection unit, reference numeral 113 denotes the filter unit, and reference numeral 114 denotes the sample.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures and functions.

This application claims the benefit of Japanese Application No. 2006-343051 filed on Dec. 20, 2006, which is hereby incorporated by reference herein in its entirety.

What is claimed is:

1. A detection device configured to detect a sample by using an electromagnetic wave including a frequency band of 30 gigahertz to 30 terahertz, the detection device comprising:

an electromagnetic-wave-generation unit constructed to generate the electromagnetic wave;

first and second electromagnetic-wave-transmission lines, wherein the first and second electromagnetic-wave-transmission lines have times of delay in propagation of the electromagnetic-wave that are different from each other;

a coupled-transmission line configured to transmit a first electromagnetic wave propagated from the first electromagnetic-wave-transmission line and a second electromagnetic wave propagated from the second electromagnetic-wave-transmission line to a single electromagnetic-wave-detection unit; and the electromagnetic-wave-detection unit, which is configured to detect the first and second electromagnetic waves propagated through the coupled-transmission line, wherein the first and second electromagnetic-wave-transmission lines and the coupled-transmission line are formed on a substrate, wherein the first electromagnetic-wave-transmission line includes a first dielectric, wherein the second electromagnetic-wave-transmission line includes a second dielectric, wherein permittivities of the first and second dielectrics are different from each other so that a difference between the propagation-delay times of the first and second electromagnetic wave-transmission lines is greater than a pulse width of the electromagnetic wave, and wherein the electromagnetic-wave-detection unit outputs time waveforms of the first and second electromagnetic waves separately.

2. The detection device according to claim 1, wherein the sample is deposited on at least one of the first and second electromagnetic-wave-transmission lines, and a change in a propagation state of the electromagnetic wave propagated through the at least one of the first and second electromagnetic-wave-transmission lines is detected.

3. The detection device according to claim 1, further comprising a liquid-storage structure configured to assist in selectively depositing a sample precipitated out of a solution on at least one of the first and second electromagnetic-wave-transmission lines.

4. The detection device according to claim 1, wherein each of the first and second electromagnetic-wave-transmission lines has at least one of a microstripline structure and a coplanar structure.

* * * * *